US009578213B2

(12) United States Patent
Moinzadeh

(10) Patent No.: US 9,578,213 B2
(45) Date of Patent: Feb. 21, 2017

(54) SURGICAL TELESCOPE WITH DUAL VIRTUAL-IMAGE SCREENS

(76) Inventor: Seyedmansour Moinzadeh, Danville, CA (US)

(*) Notice: Subject to any disclaimer, the term of this patent is extended or adjusted under 35 U.S.C. 154(b) by 844 days.

(21) Appl. No.: 13/270,065

(22) Filed: Oct. 10, 2011

(65) Prior Publication Data
US 2013/0088582 A1 Apr. 11, 2013

(51) Int. Cl.
H04N 7/18 (2006.01)
H04N 5/225 (2006.01)
G02B 27/01 (2006.01)

(52) U.S. Cl.
CPC ........... *H04N 5/2251* (2013.01); *A61B 90/361* (2016.02); *G02B 27/017* (2013.01); *A61B 2090/365* (2016.02); *A61B 2090/3616* (2016.02); *A61B 2090/502* (2016.02); *G02B 2027/0138* (2013.01); *G02B 2027/0178* (2013.01); *H04N 7/183* (2013.01); *H04N 2005/2255* (2013.01)

(58) Field of Classification Search
CPC ............... A61B 19/5212; A61B 2019/5219; A61B 90/361; A61B 2090/3616; A61B 2090/365; A61B 2090/502; H04N 5/2251; H04N 7/183; H04N 2004/2255; G03B 27/017; G02B 2027/0138; G02B 2027/0178
USPC .......................................................... 348/77
See application file for complete search history.

(56) References Cited

U.S. PATENT DOCUMENTS

| 4,621,283 | A | 11/1986 | Feinbloom |
| 4,859,032 | A | 8/1989 | Feinbloom |
| 5,189,512 | A | 2/1993 | Cameron et al. |
| 5,446,507 | A * | 8/1995 | Chang ............... G02B 7/002 351/124 |
| 5,737,013 | A | 4/1998 | Williams et al. |
| 5,971,540 | A | 10/1999 | Ofner |
| 6,065,835 | A | 5/2000 | Pekar et al. |
| 6,671,090 | B2 | 12/2003 | Luecke et al. |
| 6,731,326 | B1 | 5/2004 | Bettinardi |
| 6,890,077 | B2 | 5/2005 | Dunn |

(Continued)

OTHER PUBLICATIONS

International Search Report and Written Opinion from PCT Patent Application No. PCT/US2012/058648 mailed Mar. 25, 2013.

(Continued)

*Primary Examiner* — Gims Philippe
*Assistant Examiner* — Joseph Becker
(74) *Attorney, Agent, or Firm* — Law Office of Rodney LeRoy

(57) ABSTRACT

A surgical telescope includes a front frame configured to be positioned in front of a use's eyes, and a camera coupled to the front frame. The camera is configured to generate image information of a scene viewed by the camera. The surgical telescope further includes a circuit coupled to the camera and is configured to receive the image information from the camera and process the image information for display. The surgical telescope further includes a virtual-imaging screen disposed in the front frame and coupled to the circuit. The virtual-imaging screen is configured to: be position in front of a user's eyes, receive the image information from the circuit, and display images from image information. The surgical telescope further includes a lens positioned over the virtual-imaging screen for creating virtual images of the images displayed on the virtual-imaging screen. The virtual images are behind the virtual-imaging screen.

28 Claims, 10 Drawing Sheets

(56) References Cited

U.S. PATENT DOCUMENTS

| | | |
|---|---|---|
| 2002/0003602 A1 | 1/2002 | Burckhardt |
| 2003/0048531 A1* | 3/2003 | Luecke et al. |
| 2003/0107652 A1* | 6/2003 | Williams .................. 348/207.99 |
| 2004/0156114 A1* | 8/2004 | Sayed et al. .................. 359/630 |
| 2007/0058261 A1* | 3/2007 | Sugihara .............. G02B 6/0011 359/630 |
| 2007/0121203 A1 | 5/2007 | Riederer |
| 2010/0045783 A1* | 2/2010 | State et al. ...................... 348/53 |
| 2011/0145978 A1 | 6/2011 | Harbin |
| 2012/0119978 A1* | 5/2012 | Border ............... G02B 27/0172 345/8 |

OTHER PUBLICATIONS

"Wearable Aids," http://www.lowvisiondigest.org/wearble_aids2.htm, TechMark Communications, Inc. 2006-2007, Jul. 17, 2007, 9 pages.

\* cited by examiner

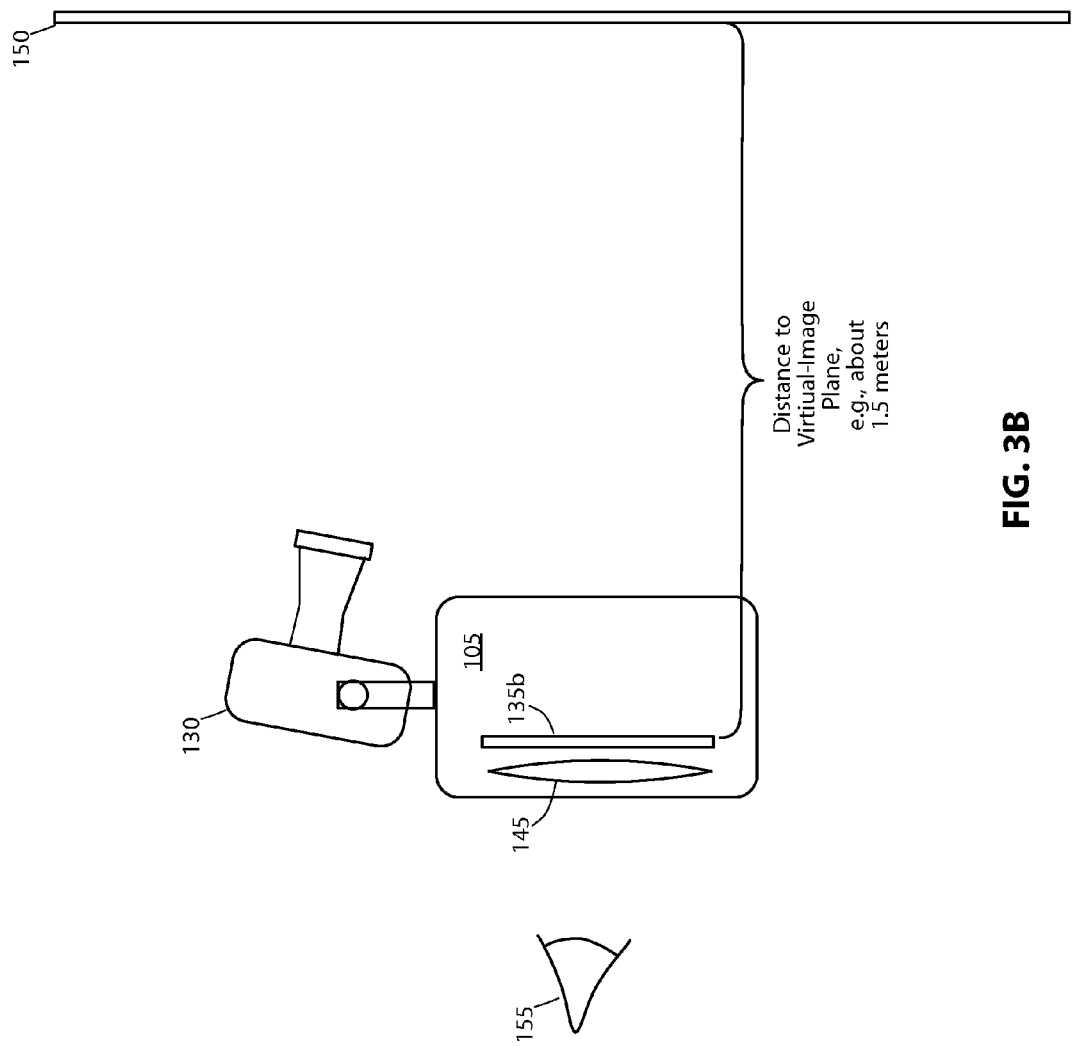

SURGICAL TELESCOPE WITH DUAL VIRTUAL-IMAGE SCREENS

BACKGROUND

The present invention generally relates to surgical telescopes, and more particularly embodiments of the present invention relate to a surgical telescope having dual virtual-image screens for comfortable viewing.

Unless otherwise indicated herein, the apparatus and methods described in the background section are not prior art to the claims in this application and are not admitted to be prior art by inclusion in the background section.

Surgical telescopes provide a magnified view of an object that a surgeon is viewing. A magnified view of an object on which a surgeon is operating aids the surgeon in performing a successful surgery. A number of design considerations exist for surgical telescopes, such as relatively high image quality and good ergonomics.

Various known surgical telescopes often trade off high image quality for low comfortable physical use, or trade off high comfortable physical use for low image quality. Known surgical telescopes are typically categorized into three different types of surgical telescopes. A first type, and first generation, of surgical telescopes includes single-lens diopter magnifiers. A second type, and second generation, of surgical telescopes includes surgical telescopes with a preset declination angle. A third type, and third generation, of surgical telescopes includes surgical telescopes having a fully adjustable declination angle. A declination angle is an angle at which a surgeon's eyes must be angled down to look through surgical telescope to see a magnified image of an object.

Surgeons using surgical telescopes often experience strain of the eyes, neck, back, shoulders and arms, and the like. The design aspects of surgical telescopes that effect these strains on the body include declination angle, depth of field and magnification, weight, field of view, frame design, and the like. A surgical telescope with a low declination angle typically provides that a surgeon eyes are similarly positioned at a low declination angle, and to look downward the surgeon must tilt her head downward, tilt her upper body (e.g., shoulders and/or back) downward, or tilt both her head and her upper body downward. A downward tilt of a surgeon's head and/or upper body may cause uncomfortable body strain. A low declination angle, however, does allow a surgeon's eyes to be at substantially the low declination angle providing for reduced strain on the eyes. In contrast a relatively higher declination angle allows for a surgeon's upper body to remain in a relatively more upright and comfortable position if looking down, but requires that a surgeon's eyes be a the higher declination angle (angled downward).

While some surgical telescopes provide for adjustable declination angle, these surgical telescopes often have other design aspects with ergonomics features, which may provide uncomfortable use. For example, various surgical telescopes often have a fixed and relatively shallow depth of field as a result of the magnification provided by the surgical telescopes. A surgeon using a surgical telescope that has a fixed and relatively shallow depth of field generally must move her head and/or body back and forth to keep objects within the depth of field as the surgeon looks at different objects, which are at different distances from the surgeon. Such back and forth movement during a surgical procedure may place physical strains on the surgeon that lead to discomfort. A surgeon might choose a surgical telescope with a wider depth of field to avoid such back and forth movement to improve comfortable use of the surgical telescope, but may have to sacrifice higher magnification for this improved comfortable use.

Thus, there is a need for improved surgical telescopes that provide good ergonomics and a relatively high depth of field with an amount of magnification needed by surgeons.

SUMMARY

The present invention generally relates to surgical telescopes, and more particularly embodiments of the present invention relate to a surgical telescope having dual virtual-image screens for comfortable viewing.

According to one embodiment of the present invention, a surgical telescope includes a front frame configured to be positioned in front of a use's eyes, and a camera coupled to the front frame. The camera is configured to generate image information of a scene viewed by the camera. The surgical telescope further includes a circuit coupled to the camera and is configured to receive the image information from the camera and process the image information for display. The surgical telescope further includes a virtual-imaging screen disposed in the front frame and coupled to the circuit. The virtual-imaging screen is configured to: be positioned in front of a user's eyes, receive the image information from the circuit, and display images from image information. The surgical telescope further includes a lens positioned over the virtual-imaging screen for creating virtual images of the images displayed on the virtual-imaging screen where the virtual images are behind the virtual-imaging screen.

According to a specific embodiment, the surgical telescope further includes a second virtual-imaging screen disposed adjacent to the first mentioned virtual-imaging screen in the front frame and coupled to the circuit. The second virtual-imaging screen is configured to: be positioned in front of a user's other eye, receive the image information from the circuit, and display images from image information. The surgical telescope further includes a second lens positioned over the second virtual-imaging screen for creating second virtual images of a the images displayed on the second virtual-imaging screen. The second virtual images are behind the second virtual-imaging screen.

According to one specific embodiment, the first mentioned virtual images and the second virtual images are one to two meters behind the first and the second virtual-imaging screens. According to another specific embodiment, the first virtual images and the second virtual images are approximately 1.5 meters behind the first and the second virtual-imaging screens, and the first virtual images and the second virtual images are on a virtual image plane. The first virtual images and the second virtual images may be video images. The first and the second virtual-imaging screens are liquid crystal virtual-imaging screens.

According to another specific embodiment, the surgical telescope further includes first and second temples coupled to the front frame and configured to position the front frame in front of a user's eyes. At least one of the first and the second temples includes a jack receptacle for receiving power to power the camera, the circuit, and the virtual-imaging screen.

According to another specific embodiment, the surgical telescope further includes a handheld magnifier configured to generate alternative image information of a scene viewed by the handheld magnifier where the circuit is coupled to the handheld magnifier to receive the image information from the handheld magnifier and process the image information for display on the virtual-imaging screen. The camera is configured to be powered off and not provide image information to the circuit if the handheld magnifier provides the alternative image information to the circuit.

The handheld magnifier is configured to be coupled to one of the first or the second temple via a wire connection to provide the alternative image information to the circuit. According to another specific embodiment, the handheld magnifier includes a light configured to light a scene viewed by the handheld magnifier. A focusing distance of the handheld magnifier is about 2 millimeters to about 2 centimeters. The handheld magnifier may be pen shaped.

According to one specific embodiment, the surgical telescope further includes a transmitter configured to transmit the image information to a computer or a network router. The image information transmitted to the network router is configured to be displayed remotely on a computer system communicatively coupled to the network router.

According to another embodiment of the present invention, a surgical telescope includes a front frame configured to be positioned in front of a use's eyes, and a handheld magnifier configured to generate image information of a scene viewed by the handheld magnifier. The surgical telescope further includes a circuit coupled to the handheld magnifier and is configured to receive the image information from the handheld magnifier and process the image information for display. The surgical telescope further includes a virtual-imaging screen disposed in the front frame and coupled to the circuit. The virtual-imaging screen is configured to: be position in front of a user's eyes, receive the image information from the circuit, and display images from image information. The surgical telescope further includes a lens positioned over the virtual-imaging screen for creating virtual images of the images displayed on the virtual-imaging screen, wherein the virtual images are behind the virtual-imaging screen.

The following detailed description and accompanying drawings provide a better understanding of the nature and advantages of the present invention.

BRIEF DESCRIPTION OF THE DRAWINGS

FIG. 3B is a simplified schematic of a side view of the front frame and the virtual image plane;

DETAILED DESCRIPTION

The present invention generally provides a surgical telescopes, and more particularly embodiments of the present invention provide a surgical telescope having dual virtual-image screens for comfortable viewing.

In the following description, for purposes of explanation, numerous examples and specific details are set forth in order to provide a thorough understanding of the present invention. It will be evident, however, to one skilled in the art that the present invention as defined by the claims may include some or all of the features in these examples alone or in combination with other features described below, and may further include modifications and equivalents of the features and concepts described herein.

Figure 1A:
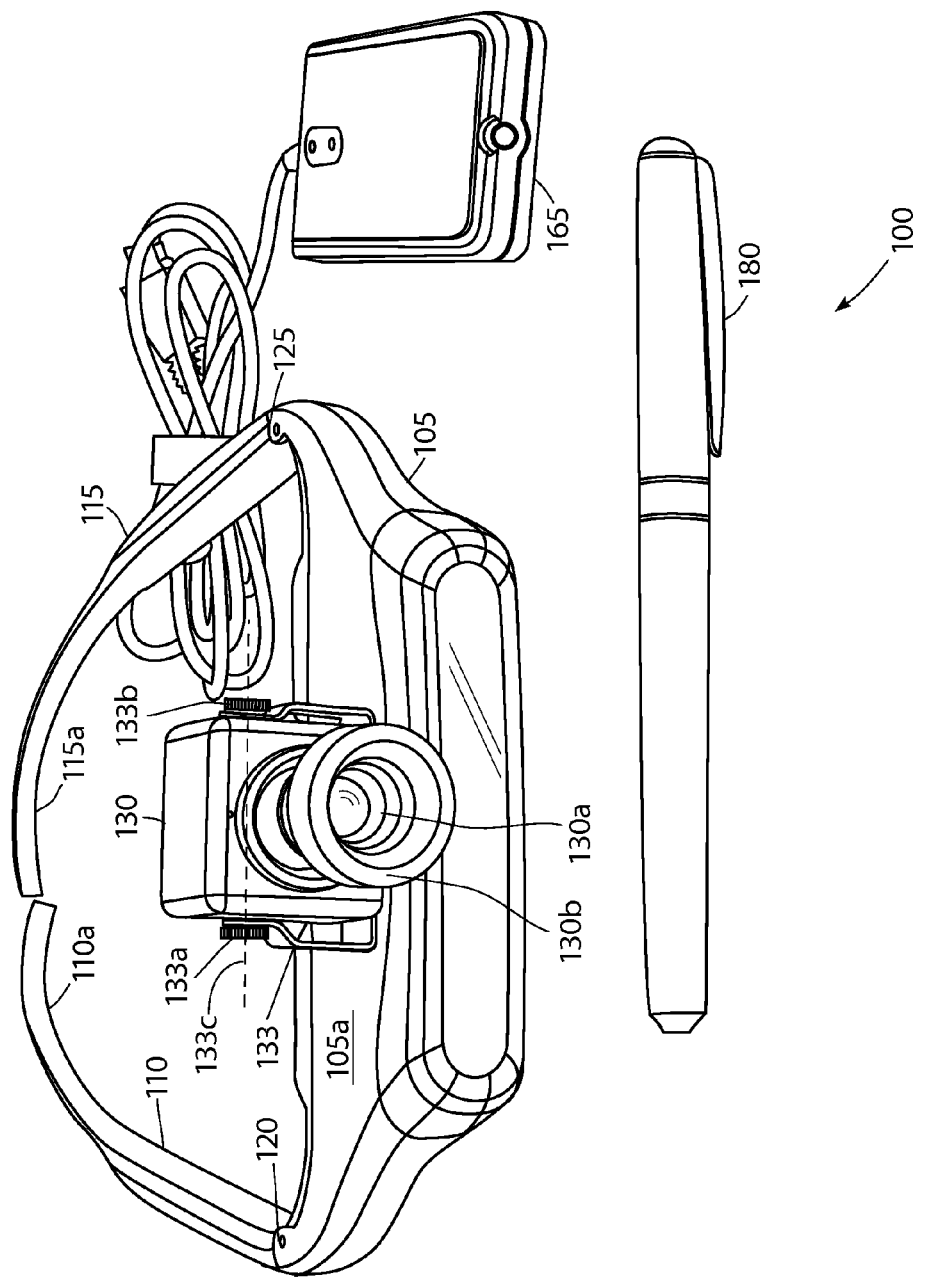
FIG. 1A is a simplified schematic of a surgical telescope according to one embodiment of the present invention.
Figure 1B:
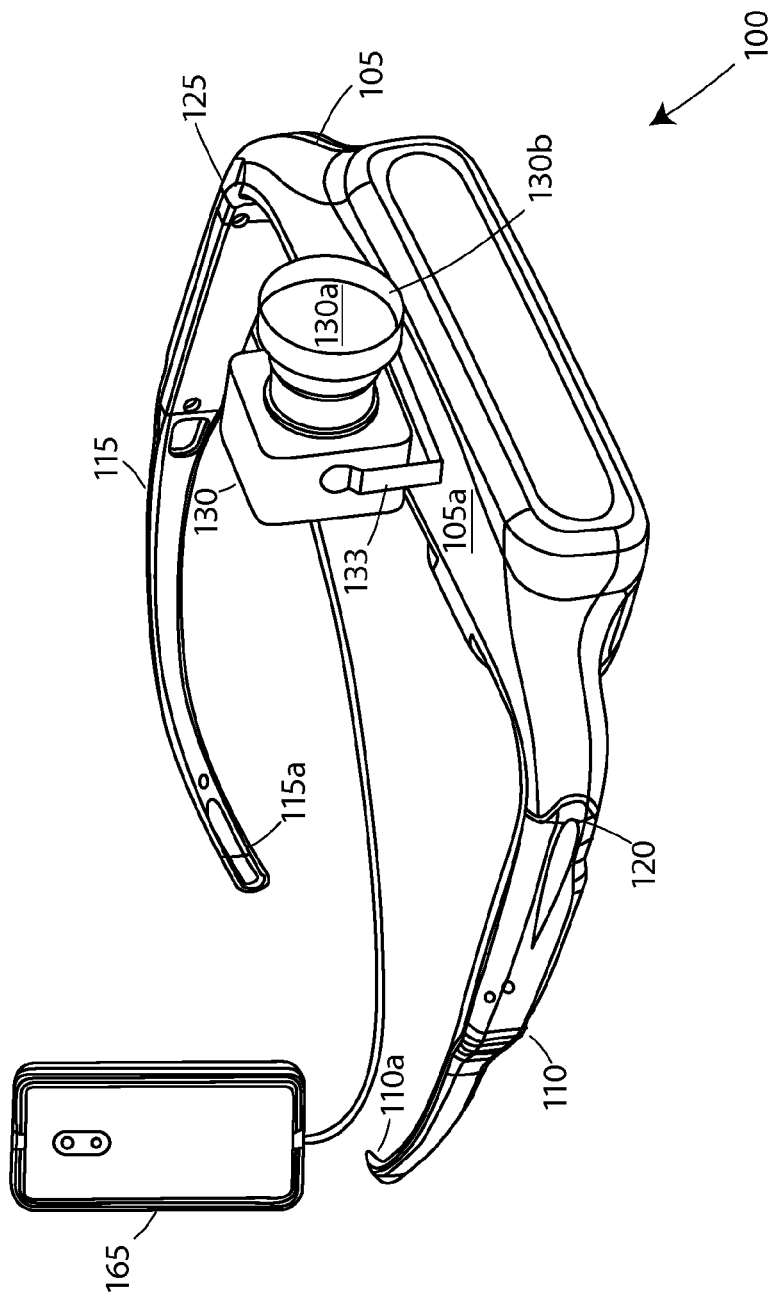
FIG. 1B is an overall perspective view of the surgical telescope.
Figure 1C:
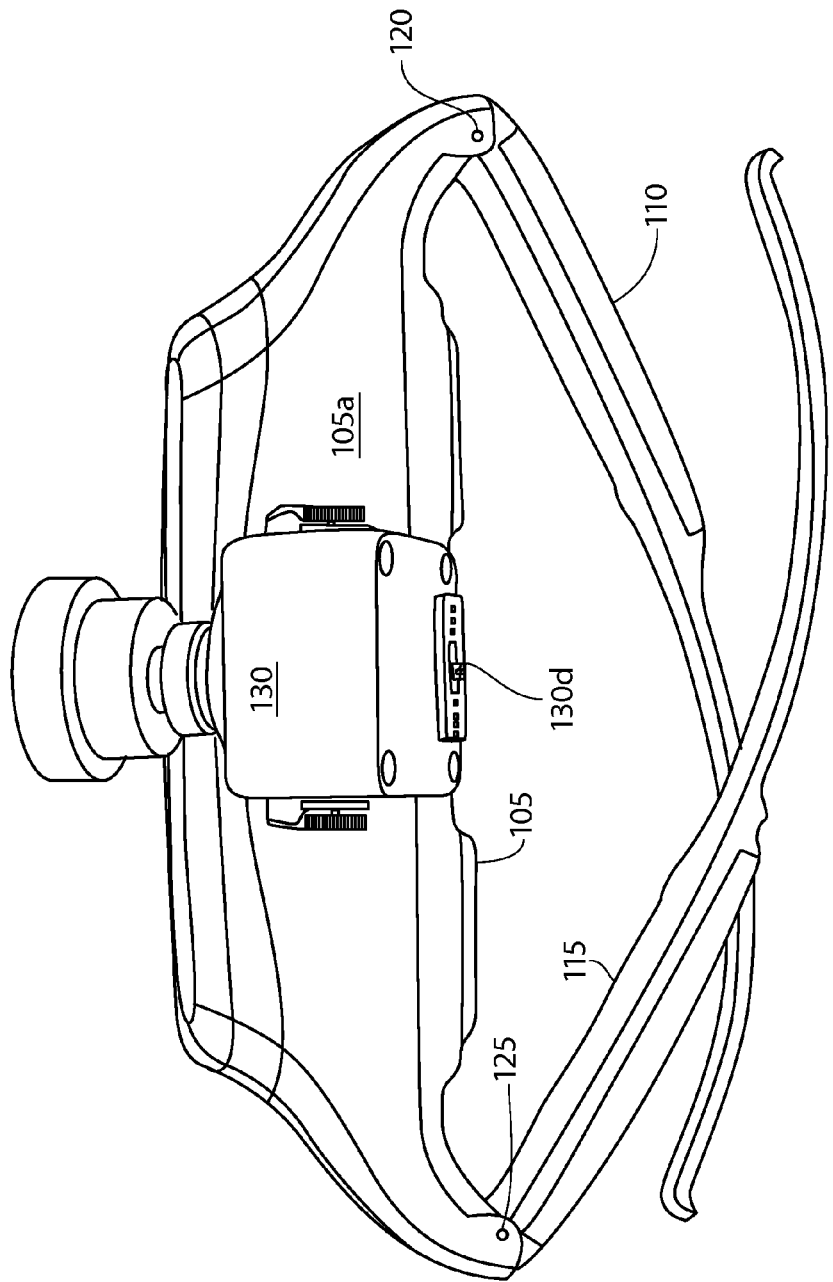
FIG. 1C is a simplified top view of the surgical telescope showing the left and the right temples folded down onto the front frame.
Figure 1D:
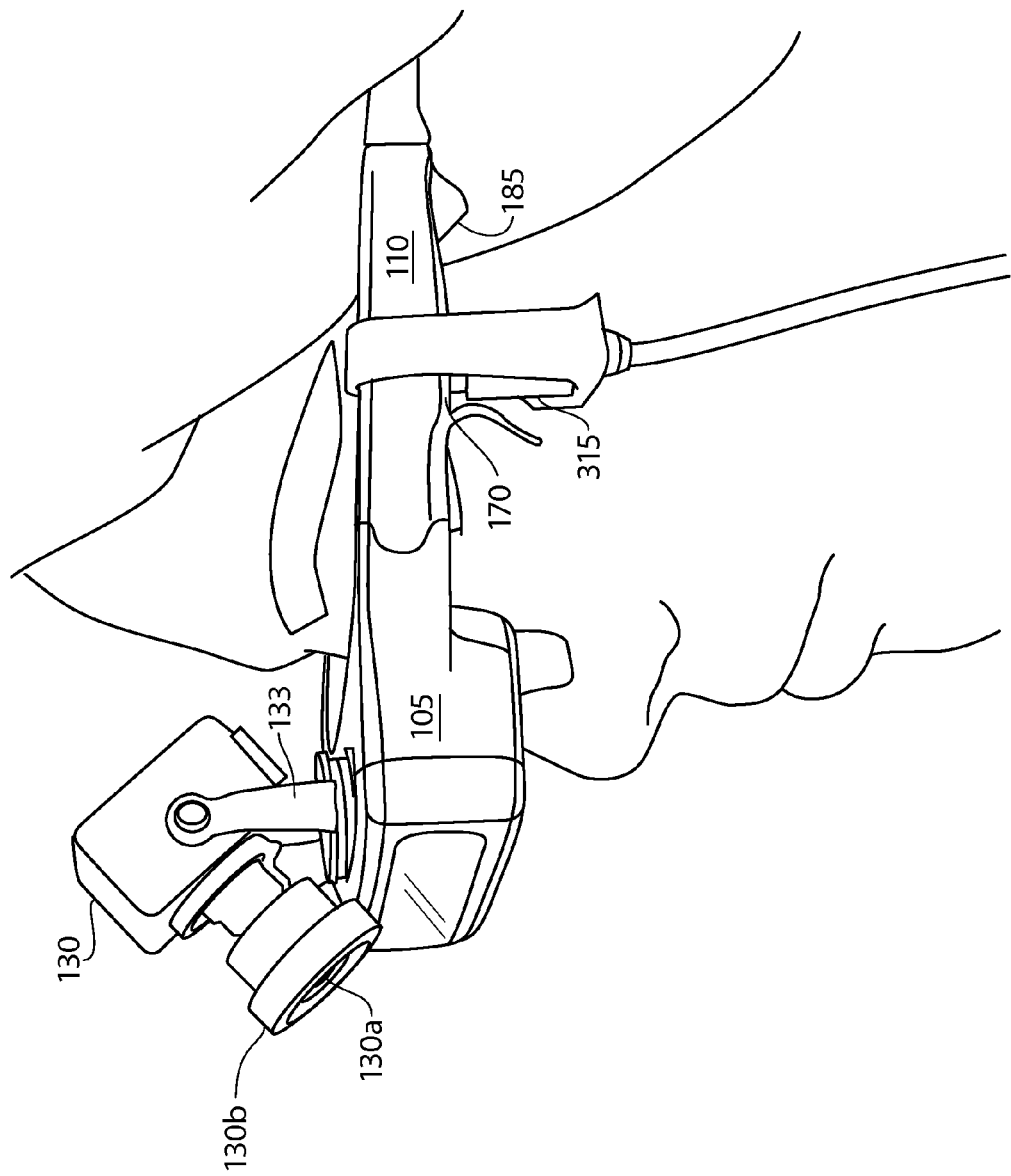
FIG. 1D is an image of a surgeon wearing the surgical telescope substantially similarly to how a surgeon may wear a pair of eye glasses.

A surgical telescope is an apparatus that a surgeon typically wears over her eyes and provides a magnified view of objects that the surgeon may be performing a surgical operation on. FIG. 1A is a simplified schematic of a surgical telescope 100 according to one embodiment of the present invention. Surgical telescope 100 is shown in an overall perspective view in FIG. 1B. Surgical telescope 100 includes a front frame 105 coupled to a left temple 110 and a right temple 115. Left temple 110 may be coupled to the front frame via a hinge 120, and right temple 115 may be coupled to the front frame via a hinge 125. Hinges 120 and 125 provide for the left temple and the right temple to rotate relative to the front frame so that the left and right temples may fold down onto the front frame. FIG. 1C is a simplified top view of surgical telescope 100 showing the left and the right temple folded down onto the front frame. The left and right temples may respectively include a left wrap 110a and a right wrap 115b where the left and the right wraps are configured to extend behind the head of a surgeon who is wearing the surgical telescope. The left and right wraps are configured to stabilize the surgical telescope on a surgeon's head. FIG. 1D is an image of a surgeon wearing surgical telescope 100 substantially similarly to how a surgeon may wear a pair of eye glasses. As shown in FIG. 1D, surgical telescope 100 may be configured to fit over a surgeon's eye glasses.

According to one embodiment, front frame 105 includes a camera 130 mounted thereto. Camera 130 may be mounted on a top surface 105a of front frame 105. While camera 130 is shown as being mounted on top surface 105a of the front frame, camera 130 may be alternatively mounted, such as mounted one of the temples, mounted on head mount system that fits onto or over the forehead, the pate, etc. of a surgeon's head. Camera 130 may be mounted to front face 105 via a camera mount 133. Camera 130 may be coupled to camera mount 133 via a set of hinges 133a and 133b. Hinges 133a and 133b provide that camera 130 may be rotated about a horizontal axis 133c passing through hinges 133a and 133b. A surgeon using surgical telescope 100 may grasp camera 130 and rotate the camera vertically about horizontal axis 133c to change the angle of view of the camera.

Camera 130 includes a set of lenses 130a and may include a focusing ring 130b. A set as referred to herein includes one or more elements. Focusing ring 130b may be configured to be rotated to focus the set of lenses 130a. For example, the focusing ring may be grasped by a surgeon using the surgical telescope and rotated to adjust the focus of the set lens 130a.

Figure 2:
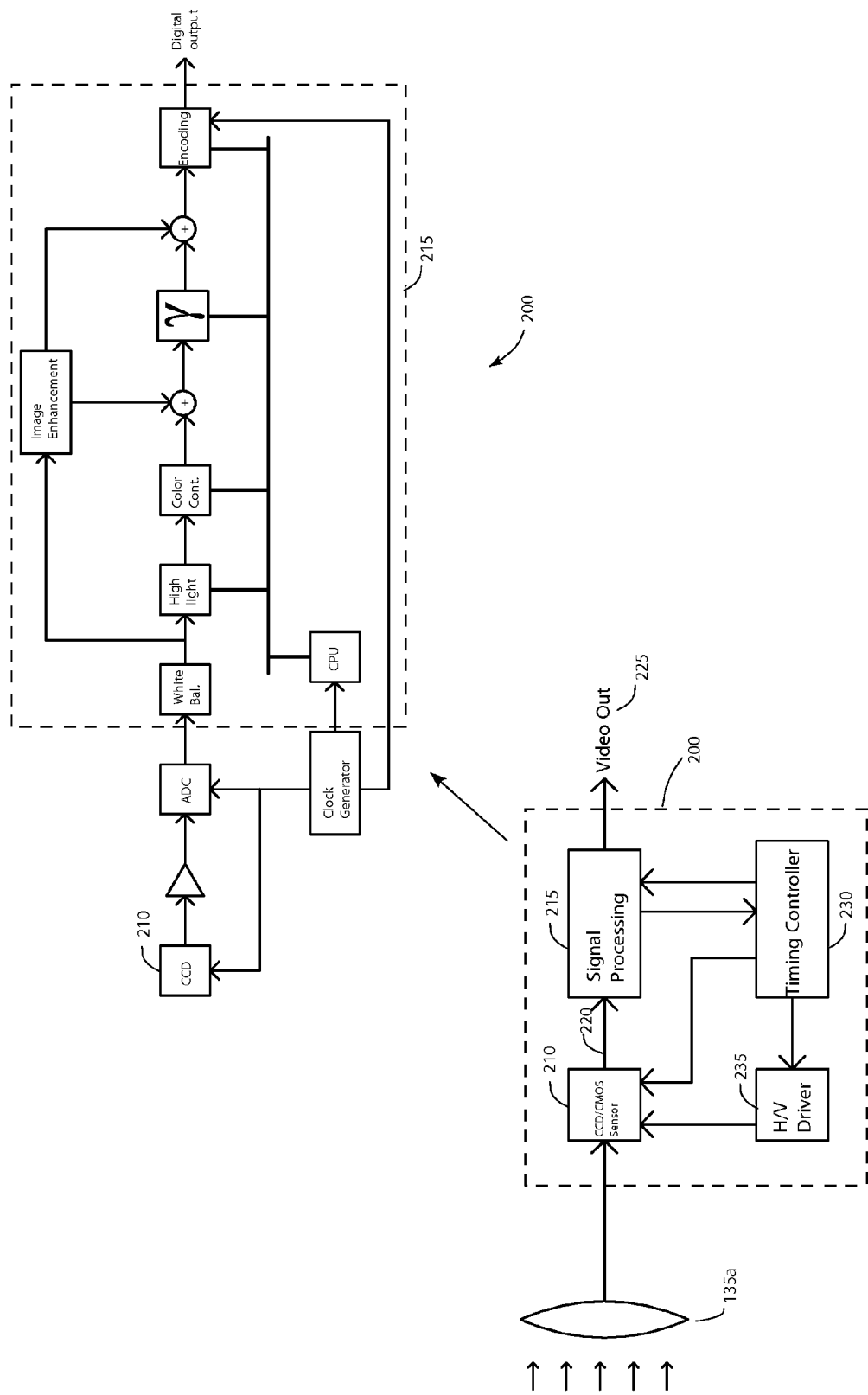
FIG. 2 is a simplified circuit diagram of a camera circuit that may be included in the camera according to one embodiment of the present invention.

FIG. 2 is a simplified circuit diagram of a camera circuit 200 that may be included in camera 130 according to one embodiment of the present invention. FIG. 2 also shows a further detailed view of circuit 200. The set of lenses 130*a* may be configured to collect light from a scene viewed the camera and supply an image (e.g., a magnified image) of the scene to an imaging array 210. Imaging array 210 may be a CCD (charge coupled device) image sensor array, a CMOS (complementary metal oxide) image senor array, or the like. According to one specific embodiment, imaging array 210 includes a CCD array having 542 horizontal rows of pixels and 582 vertical columns of pixels. According to an alternative embodiment, imaging array 210 includes a CCD array having 542 horizontal rows of pixels and 492 vertical columns of pixels. The CCD array may be approximately ¼ inch square.

Camera circuit 200 may also include a signal processing unit 215 configured to process analog image data 220 generated by the imaging array and generate an output video signal 225, which is digital. The camera circuit may include a timing controller 230 for controlling the collection of light by the imaging array and controlling a horizontal-vertical sync pulses driver 235 for the imaging array (e.g., CCD array).

The signal processor may be configured to provide a number of video operations, such as video encoding, and may encode video according to the PAL (phase alternating line) standard, the NTSC (National Television System Committee) standard, or the SECAM (squentiel couleur à mémoire) standard for analogue color encoding. A scanning system of the signal processor may control scanning of the imaging array at a 625 line system with 50 fields/second scanned, or a 525 line system with 60 fields/second scanned. A synchronization system of the signal processor may be an internal synchronization system. The minimum illumination for the imaging array may be 0.5 lux at F1.2. The vertical resolution of camera 130 may be 380 TVL (TV lines) or 470 TVL/470 TVL (enhanced). The signal to noise ratio for camera 130 may be 60 dB (TYP). For camera 130 the white balance may be auto high speed with a white balance range of 3000°-15000° K (Kelvin). The set of lenses 130*a* may include an auto iris lens (not shown) which is configured to electronically and automatically adjust to maintain relatively constant brightness (i.e., optimal brightness) in output video signals (sometimes referred to herein as image information) output from camera 130 regardless of whether the brightness of a scene viewed by the set of lenses changes. Camera 130 may also be fitted with an automatic electronic shutter (AES) which is configured to perform the same function as the auto iris lens of providing constant brightness in output video signals. The AES provides for constant brightness by adjusting the shutter speed up or down automatically to adjust for changing brightness in a scene viewed by the camera. The auto iris function of the auto iris lens and the AES function of the AES are typically not configured to operate simultaneously. One or the other of these systems will operate to adjust for the brightness in output video signals. According to a further embodiment, the video signal output from the camera is 1.0 volts peak-to-peak composite video with a 75 ohm termination. Gamma correction for camera 130 is typically about 0.45. Camera 130 may also be configured for automatic gain control to further provide that the brightness of the output video signal does not vary. Camera 130 may be configured to operate at 5 volts DC and a 160 milliamp draw. Many of the foregoing described operations of camera 130 are well understood by those of skill in the video arts and are not described in detail herein.

Figure 3A:
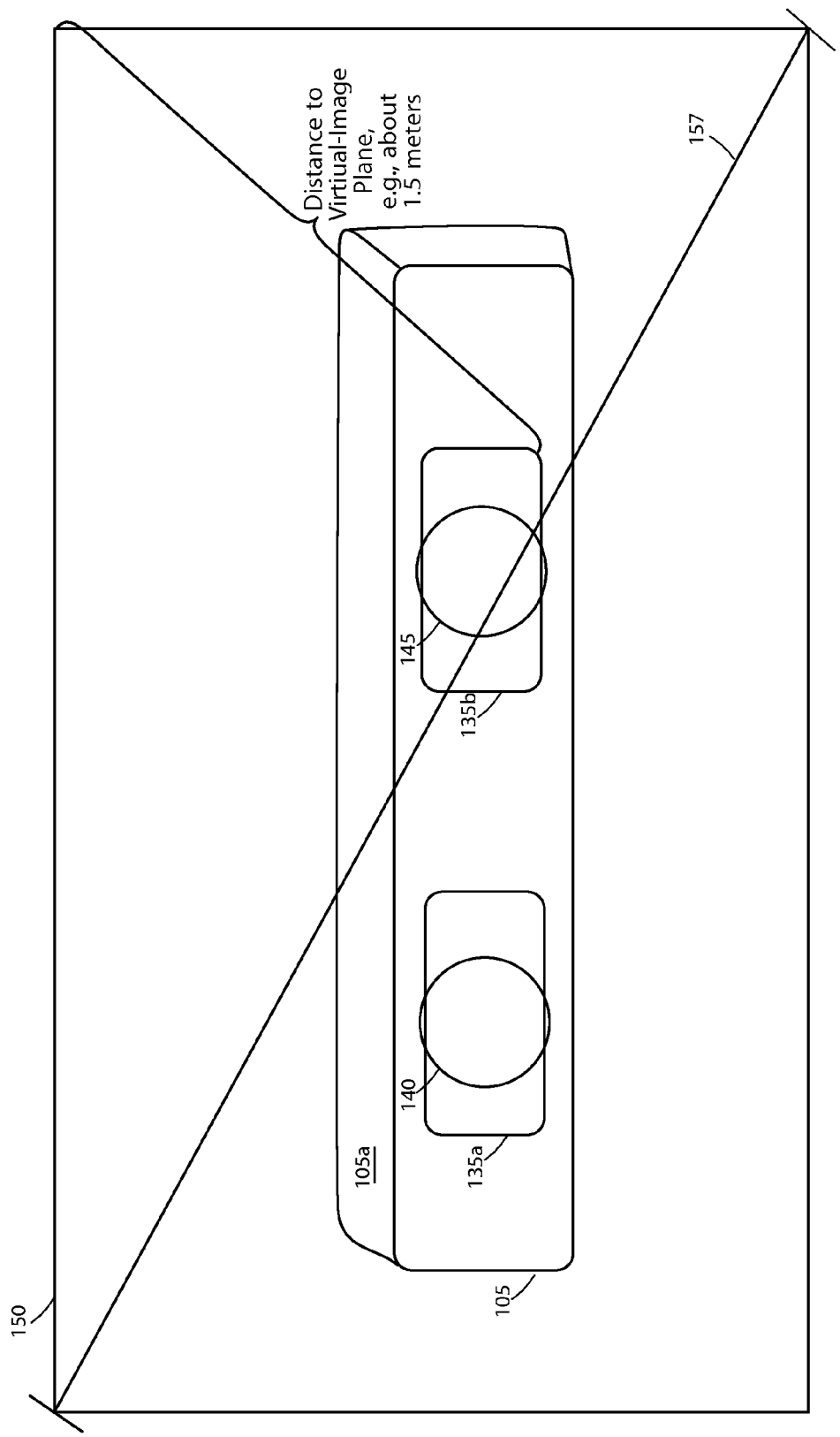
FIG. 3A is a simplified schematic of surgical telescope showing a back of the surgical telescope.

FIG. 3A is a simplified schematic of front frame 105 of surgical telescope 100 showing a back of the front frame. The back view of front frame 105 shows a view of the surgical telescope from that of a surgeon wearing the surgical telescope. According to one embodiment of the present invention, front frame 105 and surgical telescope 100 includes at least a first virtual-imaging screen 135*a* and may include a second virtual-imaging screen 135*b*. The output video signal generated by camera 130 and processed by circuit 200 is supplied to the set of virtual-imaging screens for display of the output video signal on the set of virtual-imaging screens. Each virtual-imaging screen may be a liquid-crystal display (LCD), such as a thin film transistor (TFT) LCD. According to one embodiment each virtual-imaging screen includes an active array of pixels that is 640×480 pixels. The aspect ratio provided by each virtual-imaging screen is 4:3. The color depth of the virtual-imaging arrays may be 24 bit. The view angle of the virtual-imaging screens is 35 degrees diagonal. The virtual-imaging screens may be configured to display composite video and may be configured to detect a format (e.g., PAL, NTSC, SECAM, etc.) of video supplied to the virtual-imaging screens for proper display of the video.

According to one embodiment, surgical telescope 100 includes a first set of lenses 140 positioned in "front" of virtual-imaging screen 135*a* and a second set of lenses 145 positioned in front of virtual-imaging screen 135*b*. That is, each set of lenses is positioned such that each set of lenses may be between one of the virtual-imaging screens and an eye of a surgeon using the surgical telescope. Each set of lenses 140 and 145 may include one or more lenses. Each set of lenses is configured to focus an image displayed on one of the virtual-imaging screens for viewing by a surgeon using the surgical telescope.

The virtual-imaging screens and the sets of lenses 140 and 145 are configured to provide a virtual-image plane 150 for displayed video where the virtual-image plane is "behind" the virtual-imaging screens. That is, the virtual-imaging screens and the sets of lenses 140 and 145 are configured to be between a surgeon's eyes 155 and the virtual-image plane 150; see FIG. 3B, which is a side view of front frame 105 and virtual-image plane 150. For example, the virtual-image plane may be about 1 meter to about 2 meters behind the virtual-imaging screens, and according to one specific embodiment, the virtual-image plane is about 1.5 meters behind the virtual-imaging screens. Providing a virtual-image plane a given distance (e.g., about 1.5 meters) behind the virtual-imaging screens provides that a surgeon's eyes may operate at a comfortable focusing distance thereby limiting strain on the surgeon eye's during use of the surgical telescope. Further, providing that the virtual-image plane at a given distance behind the virtual-imaging screens provides that angle of convergence of a surgeon's eyes may be relatively neutral and comfortable. That is, the surgeon's eyes will not be substantially crossed nor substantially divergent so as to further provide for limited eye strain during use of the surgical telescope. The distance of the virtual-image plane from the virtual-imaging screens may be predetermined and set by the sets of lenses 140 and 145. A virtual-display size 157 (indicated by a diagonal line in FIG. 3A) of a virtual image displayed by the virtual-image screens may appear as a 50 inch (diagonal) to 80 inch (diagonal) display to a surgeon using the surgical telescope.

According to one embodiment of the present invention, surgical telescope 100 includes a power source 165 as shown in FIG. 1. Power source 165 may be configured to power the camera, the camera circuit, and the virtual-imaging screens.

Figure 4:
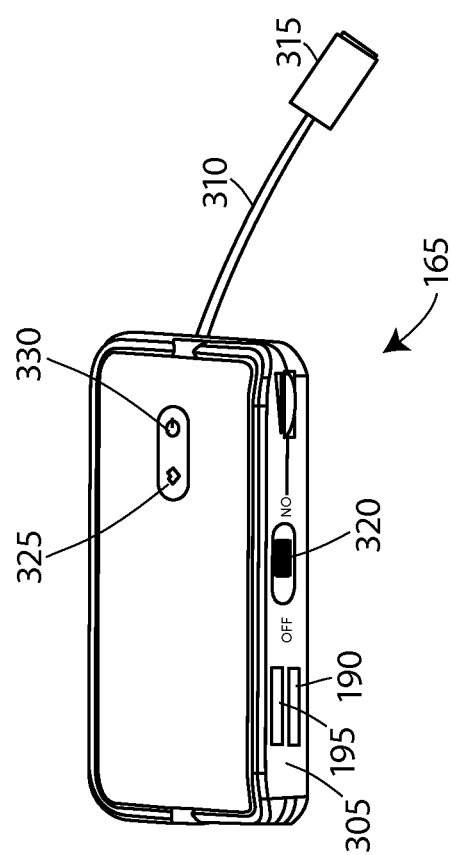
FIG. 4 is a simplified schematic of a power source according to one embodiment of the present invention.

FIG. 4 is a simplified schematic of power source 165 according to one embodiment of the present invention. Power source 165 includes a battery case 305 and a wire 310 extending from the battery case 305 to a jack 315. According to one embodiment, one or both of left temple 110 and right temple 115 may include a jack receptacle 170 (see FIG. 1D) formed therein and configured to receive jack 315 for powering the surgical telescope. Battery case 305 may be configured to house a set of rechargeable batteries or a set of disposable batteries. A rechargeable battery housed by battery case 305 may be a 5V, 1000 milliamp-hour lithium-ion battery or the like. According to one embodiment of the present invention, the power consumption of the surgical telescope may be less than about 1.1 watts.

Battery case 305 may also include a power switch 320 configured to control the supply of power to the surgical telescope. The battery case may include a charge lamp 325, which indicates the charge state of the set of batteries. The battery case may also include a power indicator 330 that indicates that the power switch is on and that the power source is supplying power to the surgical telescope. The battery case may also include a jack receptacle (not shown) configured to accept a jack for charging (e.g., "wall" charging) the set of batteries in the battery case.

Figure 5:
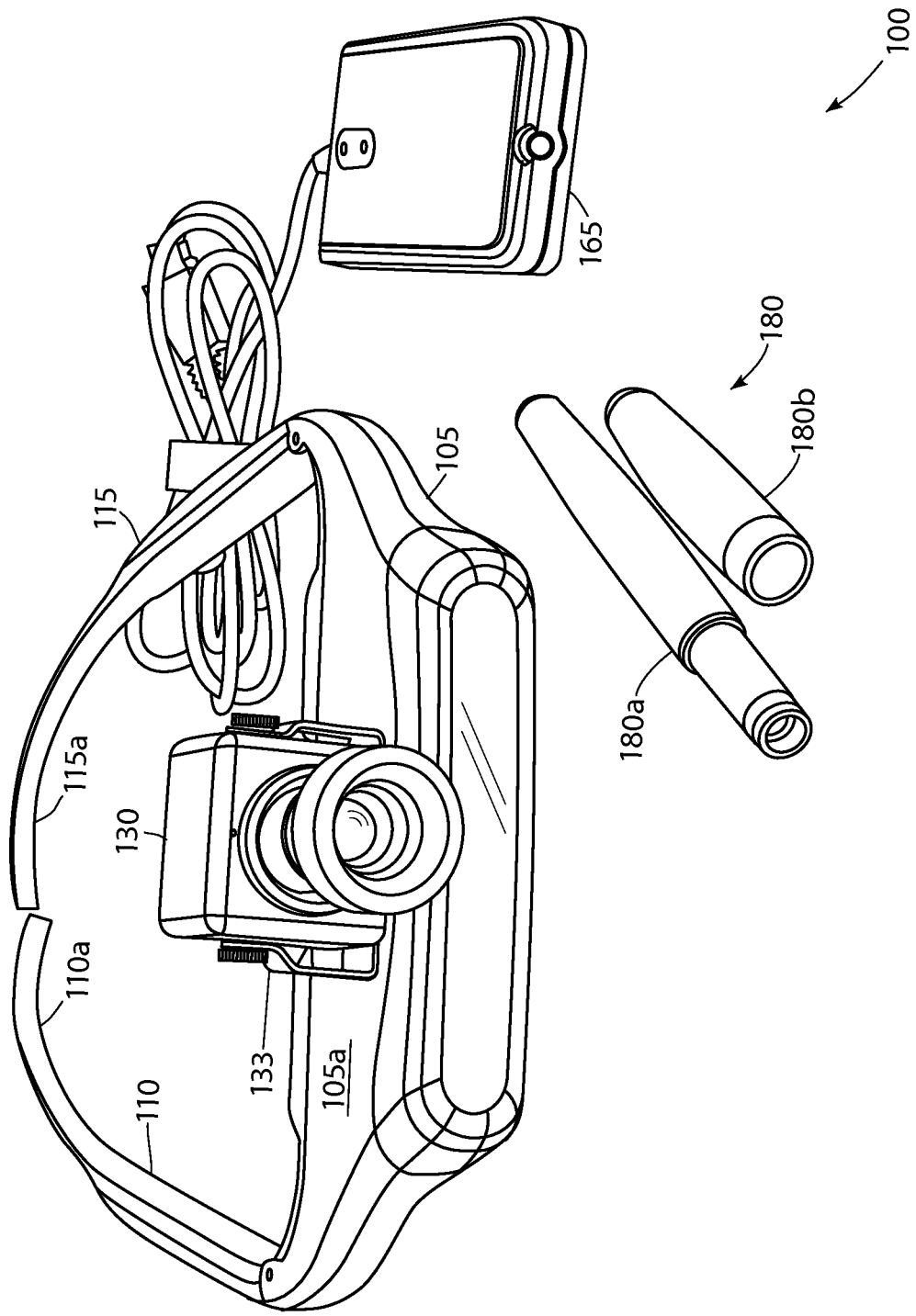
FIG. 5 is a simplified schematic of the handheld magnifier showing cap removed from a body of the handheld magnifier.

According to one embodiment, surgical telescope 100 includes a handheld magnifier 180. Handheld magnifier 180 is configured to provide relatively close-up images of objects to the virtual-imaging screens. According to one embodiment, the handheld magnifier may be substantially pen shaped. Handheld magnifier may include a body 180a and a removable cap 180b. FIG. 5 is a simplified schematic of the handheld magnifier showing cap 180b removed from body 180a.

Handheld magnifier 180 may include a set of light gathering elements 180c configured to collect light from an object for imaging the object. The set of light gathering elements may include an imaging array, such as a CCD array, a CMOS array, or the like. According to one embodiment, the set of light gathering elements includes a ⅛ inch square CMOS array having 320×240 effective pixels. A horizontal resolution of the CMOS array may be 240 TVL. The CMOS array may be configured to inter-sync and may have a signal to noise ratio of 42 dB. According to one embodiment, handheld magnifier 180 is configured to generate a video signal NTSC (National Television System Committee) video with a CVBS (composite vertical blanking signal). The gamma attenuation of the CMOS array may be 0.45 and the video signal output from the imaging array is 1.0V peak-to-peak with 75 ohm attenuation. According to one embodiment, the set of light gathering elements 180c may include one or more lenses to focus gathered light onto the imaging array.

A vision angle of the imaging array may be 90 degrees. That is, the imaging array is configured to image objects that are substantially in front of the imaging array.

Figure 6:
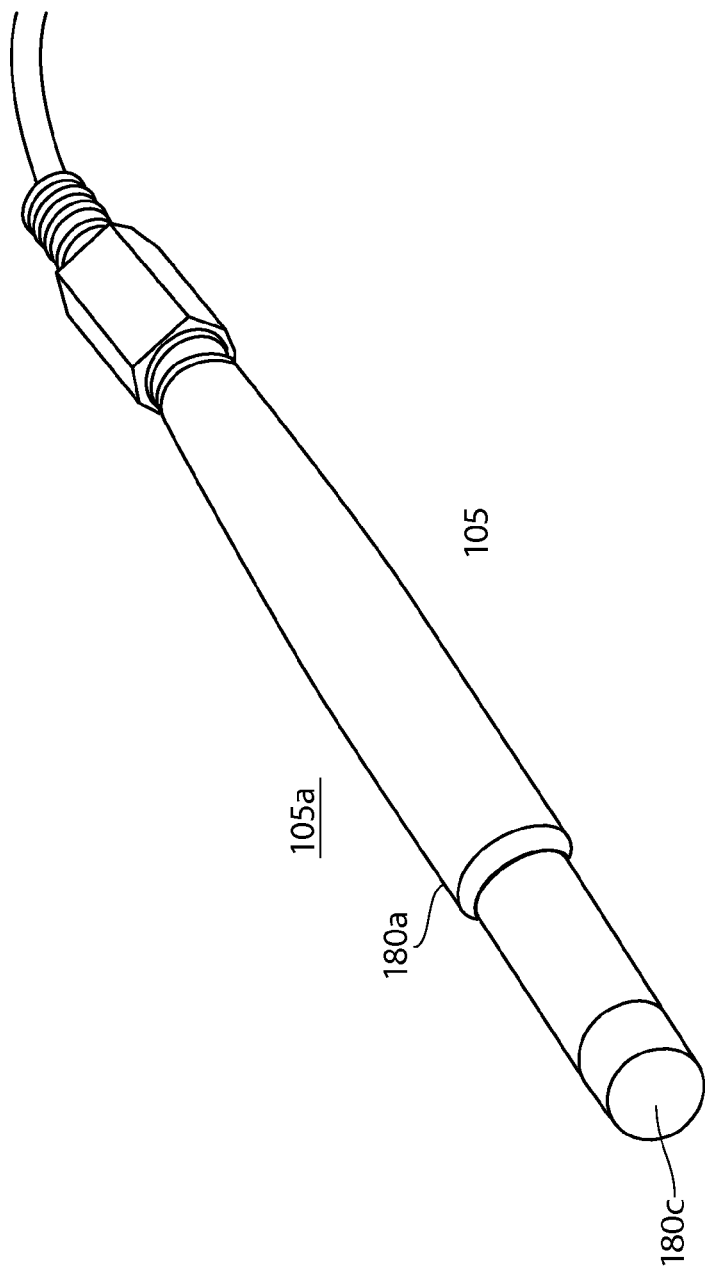
FIG. 6 is a simplified schematic of the handheld magnifier coupled to a wire, which is configured to transmit generated video to the virtual-imaging array.

The handheld magnifier may be configured to be coupled to one of the temples or the front frame via a wired connection to transmit image information to circuit 200 for display on the virtual-imaging arrays. According to one specific embodiment, left temple 110 includes a jack receptacle 185 configured to receive a jack of the handheld magnifier for receiving image information from the handheld magnifier. According to one alternative embodiment, right temple 115 may include a jack receptacle for receiving the jack of the handheld magnifier. According to another alternative embodiment, the front frame may include a jack receptacle for accepting the jack of the handheld magnifier for receiving image information from the handheld magnifier. FIG. 6 is a simplified schematic of the handheld magnifier coupled to a wire, which is configured to transmit image information to circuit 200 for display on the virtual-imaging arrays. The handheld magnifier may be configured to draw power from power supply 165 via jack receptacle 185 for powering the handheld magnifier. The handheld magnifiers may be powered by a set of batteries housed in the handheld magnifier or power may be provided to the handheld magnifier via the wire connection to the temples or the front frame. The handheld magnifier may be configured for 5V DC power and may be configured to draw 30 mA for operation.

According to one embodiment, the handheld magnifier includes a light source formed therein for illumination an object, which is being viewed by the handheld magnifier. The light source may be a light emitting diode (LED), a miniature incandescent light, or the like. An LED light source me be included in a circuit that includes imaging array 180c of the handheld magnifier. The focusing distance of the handheld magnifier may be about 2 millimeters to about two centimeters. The handheld magnifier may be relatively small and may be manipulable by a surgeon to move the handheld magnifier relatively close to objects for viewing. According to one embodiment, camera 130 includes a power switch 130d configured to power off the camera. The camera may be configured to be powered off if the handheld magnifier is coupled to the temples or the front frame. According to one alternative, circuit 200 may include a detector and power switch configured to detect the coupling of the handheld magnifier to the temples or the front frame and power down the camera if the detector detects the handheld magnifier.

According to another embodiment, image information, such as video information, generated by camera 130 and/or generated by handheld magnifier 180 is recorded for subsequent viewing. According to one embodiment, the surgical telescope includes a memory for recording image information. The front frame, one of the temples, or the power source 165 may include a memory 190 (see FIG. 4) for recording image information. The memory might be a solid state memory and may be included in circuit 200. For example, the memory might be a SIM device or the like. Alternatively, the power source might include a miniature hard disk drive or the like for recording image information. Alternatively, the surgical telescope may be configured to transmit the image information to an external memory for recording. The image information may be transmitted from the surgical telescope via a wired or a wireless communication link. For example, the front frame, one of the temples, or the power source may include a transmitter 195 (see FIG. 4), such as a radio frequency (RF) transmitter, for transmitting the image information to a local computer or the like, which is configured to store in a memory (solid state memory, disk drive, etc.) the image information transmitted from the surgical telescope. Transmitter 195 may operating according to a variety of standards, such as Bluetooth, HomeRF, etc. According to a further alternative, the image information generated by the transmitted (via a wired or wireless communication link) to a monitor or computer coupled to a monitor so that the monitor may display the image information (e.g., video derived from the image information) so that others may view the video as the surgeon is operating. For example, the video may be displayed to students, other surgeons, the patient, etc. for viewing while the surgery is being conducted. For example, image information displayed on a monitor may be viewed by students as a teaching device for teaching the students about specific surgical procedures.

According to another embodiment, transmitter 195 may be a network transmitter (e.g., a WiFi transmitter) and may be configured to transmit the image information to a network receiver (e.g., a wireless network router) to direct the image information to a network server (i.e., a server computer operating a server operating system). The network server may be configured to direct the transmission of the image information to one or more computers running a computer application for displaying images (e.g., video) derived from the image information. The computers running the computer applications may provide that users of these computers may view a surgery as a surgeon is performing the surgery while using the surgical telescope. According to one embodiment, the network server may be configured to store the image information is a mass storage device or the like for subsequent retrieval and viewing.

The above description illustrates various embodiments of the present invention along with examples of how aspects of the present invention may be implemented. The above examples and embodiments should not be deemed to be the only embodiments, and are presented to illustrate the flexibility and advantages of the present invention as defined by the following claims. For example, while embodiments of the present invention are described as including temples to attach the front from to a surgeon's head, alternative embodiments may include straps or the like for attaching the front frame to a surgeons head and all described components included in the temples may be included in the front frame, the camera, and/or the like. Further, while the above detailed description describes use of the surgical telescope embodiments by surgeons, the surgical telescope embodiments described herein may be used by dentists or other medical professional or by professionals in other fields, such as non-medical fields. $_{13}$Based on the above disclosure and the following claims, other arrangements, embodiments, implementations and equivalents will be evident to those skilled in the art and may be employed without departing from the spirit and scope of the invention as defined by the claims.

What is claimed is:

1. A device comprising:
a surgical telescope comprising:
a front frame configured to be positioned in front of a use's eyes;
a camera coupled to the front frame and configured to generate image information of a scene viewed by the camera;
a circuit coupled to the camera and configured to receive the image information from the camera and process the image information for display;
an imaging screen disposed in the front frame and coupled to the circuit, wherein the imaging screen is configured to:
be positioned in front of a user's eyes,
receive the image information from the circuit, and
display images from the image information; and
a lens positioned over the imaging screen, between the imaging screen and the position in front of a user's eye, and adapted to refract light emitted from the imaging screen for focusing the images displayed on the imaging screen and creating virtual images of the images displayed on the imaging screen, wherein the virtual images created by the lens by refraction of light emitted from the imaging screen are behind the imaging screen, the virtual images that are created by the first lens are on a virtual image plane that is generated by the first lens via refraction of the light emitted from the imaging screen, the virtual image plane is one to two meters behind the imaging screen, the virtual images have a virtual display shape in the virtual image plane that is a substantially rectangular shape, and a diagonal of the substantially rectangular shape is one hundred twenty-seven centimeters or greater.

2. The device of claim 1, further comprising:
a second imaging screen disposed adjacent to the first mentioned imaging screen in the front frame and coupled to the circuit, wherein the second imaging screen is configured to:
be positioned in front of a user's other eye,
receive the image information from the circuit, and
display images from the image information; and
a second lens positioned over the second imaging screen, between the second imaging screen and the position in front of a user's other eye, and adapted to refract light emitted from the imaging screen, focusing the images displayed on the imaging screen and for creating second virtual images of images displayed by the second imaging screen, wherein the second virtual images created by the second lens by refraction of light emitted from the second imaging screen are behind the second imaging screen in the virtual image plane.

3. The device of claim 2, wherein the second virtual images created by the second lens, via refraction of the light emitted by the second imaging screen, are one to two meters behind the first and the second imaging screens.

4. The device of claim 2, wherein the first mentioned virtual images and the second virtual images are approximately 1.5 meters behind the first and the second imaging screens.

5. The device of claim 1, wherein the diagonal of the substantially rectangular shape of the virtual image plane is two hundred three centimeters or less.

6. The device of claim 2, wherein the first mentioned virtual images and the second virtual images are video images.

7. The device of claim 2, wherein the first and the second imaging screens are liquid crystal imaging screens.

8. The device of claim 1, further comprising first and second temples coupled to the front frame and configured to position the front frame in front of a user's eyes.

9. The device of claim 8, wherein at least one of the first and the second temples includes a jack receptacle for receiving power to power the camera, the circuit, and the imaging screen.

10. The device of claim 1, further comprising a handheld magnifier configured to generate alternative image information of a scene viewed by the handheld magnifier; wherein the circuit is coupled to the handheld magnifier to receive the alternative image information from the handheld magnifier and process the alternative image information for display on the imaging screen.

11. The device of claim 10, wherein the camera is configured not to provide image information to the circuit if the handheld magnifier provides the alternative image information to the circuit.

12. The device of claim 10, further comprising first and second temples coupled to the front frame and configured to position the front frame in front of a user's eyes, wherein the handheld magnifier is configured to be coupled to one of the first or the second temple via a wire connection to provide the alternative image information to the circuit.

13. The device of claim 10, wherein the handheld magnifier includes a light configured to light a scene viewed by the handheld magnifier.

14. The device of claim 10, wherein a focusing distance of the handheld magnifier is about 2 millimeters to about 2 centimeters.

15. The device of claim 10, wherein the handheld magnifier is pen shaped.

16. The device of claim 10, further comprising a transmitter configured to transmit the image information to a computer or a network router.

17. The device of claim 16, wherein the image information transmitted to the network router is configured to be displayed remotely on a computer system communicatively coupled to the network router.

18. A device comprising:
 a surgical telescope comprising:
  a front frame configured to be positioned in front of a use's eyes;
  a handheld magnifier configured to generate image information of a scene viewed by the handheld magnifier;
  a circuit coupled to the handheld magnifier and configured to receive the image information from the handheld magnifier and process the image information for display;
  an imaging screen disposed in the front frame and coupled to the circuit, wherein the imaging screen is configured to:
  be positioned in front of a user's eyes,
  receive the image information from the circuit, and
  display images from the image information; and
  a lens positioned over the imaging screen, between the imaging screen and the position in front of the user's eye, and adapted to refract light emitted from the imaging screen for focusing the images displayed on the imaging screen and creating virtual images of the images displayed on the imaging screen, wherein the virtual images created by the lens by refraction of light emitted from the imaging screen are behind the imaging screen, the virtual images that are created by the first lens are on a virtual image plane that is generated by the first lens via refraction of the light emitted from the imaging screen, the virtual image plane is one to two meters behind the imaging screen, the virtual images have a virtual display shape in the virtual image plane that is a substantially rectangular shape, and a diagonal of the substantially rectangular shape is one hundred twenty-seven centimeters or greater.

19. The device of claim 2, wherein the imaging screen, the lens, and the position in front of a user's eye from which the virtual images are viewed are arranged in a first straight line, and the second imaging screen, the second lens, and the position in front of a user's other eye from which the second virtual images are viewed are arranged in a second straight line.

20. The device of claim 8, wherein a diagonal of the substantially rectangular shape is one hundred twenty-seven centimeters or greater.

21. The device of claim 8, further comprising first and second temples coupled to the front frame and configured to position the front frame in front of a user's eyes, wherein the handheld magnifier is configured to be coupled to one of the first or the second temples via a wire connection to provide the image information to the circuit.

22. The device of claim 8, wherein the handheld magnifier includes a light configured to light a scene viewed by the handheld magnifier.

23. The device of claim 8, wherein a focusing distance of the handheld magnifier is about 2 millimeters to about 2 centimeters.

24. The device of claim 8, further comprising:
 a second imaging screen disposed adjacent to the first mentioned imaging screen in the front frame and coupled to the circuit, wherein the second imaging screen is configured to:
  be positioned in front of a user's other eye,
  receive the image information from the circuit, and
  display images from the image information; and
 a second lens positioned over the second imaging screen, between the second imaging screen and the position in front of the user's other eye, and adapted to refract light emitted from the imaging screen, focusing the images displayed on the imaging screen and for creating second virtual images of images displayed by the second imaging screen, wherein the second virtual images created by the second lens by refraction of light emitted from the second imaging screen are behind the second imaging screen in the virtual image plane.

25. The device of claim 8, further comprising a transmitter configured to transmit the image information to a computer or a network router.

26. The device of claim 25, wherein the image information transmitted to the network router is configured to be displayed remotely on a computer system communicatively coupled to the network router.

27. The device of claim 20, wherein the diagonal of the substantially rectangular shape of the virtual image plane is two hundred three centimeters or less.

28. The device of claim 24, wherein the imaging screen, the lens, and the position in front of a user's eye from which the virtual images are viewed are arranged in a first straight line, and the second imaging screen, the second lens, and the position in front of a user's other eye from which the second virtual images are viewed are arranged in a second straight line.

* * * * *